United States Patent [19]

Canavesi et al.

[11] 4,306,104

[45] Dec. 15, 1981

[54] PROCESS FOR THE PREPARATION OF CHLOROBENZENE

[75] Inventors: Roberto Canavesi, Bollate; Roberto Ghezzi, Cusano Milanino; Giorgio Podestá, Lomagna, all of Italy

[73] Assignee: Euteco S.p.A., Milan, Italy

[21] Appl. No.: 828,998

[22] Filed: Aug. 30, 1977

[30] Foreign Application Priority Data

Oct. 5, 1976 [IT] Italy .................................. 27992 A/76

[51] Int. Cl.³ ............................................ C07C 17/12
[52] U.S. Cl. ................................... 570/203; 252/463
[58] Field of Search ................... 260/650 R; 252/463; 570/203

[56] References Cited

U.S. PATENT DOCUMENTS

| | | | |
|---|---|---|---|
| 1,963,761 | 6/1934 | Prahl | 260/650 R |
| 3,297,588 | 1/1967 | Kehl et al. | 252/463 |
| 3,345,422 | 10/1967 | Piester et al. | 260/650 R |
| 3,363,010 | 1/1968 | Schwarzenbek | 260/650 R |
| 3,950,443 | 4/1976 | Prahl | 26 0/650 R |
| 3,986,984 | 10/1976 | Michalko | 252/463 |

FOREIGN PATENT DOCUMENTS 942841 11/1963 United Kingdom ............... 252/463

Primary Examiner—Delbert E. Gantz
Assistant Examiner—Joseph A. Boska
Attorney, Agent, or Firm—Christie, Parker & Hale

[57] ABSTRACT

Chlorobenzene is produced by contacting a gaseous flow comprising benzene, oxygen and a halogenating agent, at a temperature of from 190° to 230° C., with a fluidized bed of catalyst particles comprising copper chloride deposited on an eta alumina support having a total volume of pores of from 0.3 to 0.5 ml/g and a surface area of from 250 to 400 m²/g.

8 Claims, No Drawings

PROCESS FOR THE PREPARATION OF CHLOROBENZENE

The present invention relates to the production of chlorobenzene by oxychlorination of benzene.

Chlorobenzene may be used as a solvent, for the manufacture of phenol or DDT and as an intermediate for the manufacture of dyes.

According to a known process chlorobenzene is prepared by feeding gaseous chlorine into liquid benzene in the presence of a catalyst chosen from metallic chlorides and iodine.

According to another known process a gaseous flow containing benzene, hydrogen chloride and oxygen is fed over a catalyst containing copper.

In the liquid phase process chlorine is required as the halogenating agent and moveover this process presents disadvantages due to the production of hydrogen chloride as a by-product.

In the gaseous phase process a non-negligible amount of benzene is transformed into total oxidation products and the reasons for the low selectivity are mainly sought in the difficulty of controlling the temperature.

The use of tube bundle reactors has not resulted in an increase in the selectivity to completely satisfactory values and has introduced complications in carrying out the process.

These drawbacks are overcome by the process of the invention, in which a catalyst of improved activity and mechanical properties is used.

Thus, the invention provides a process for the production of chlorobenzene, characterized by contacting a gaseous flow comprising benzene, oxygen and a halogenating agent chosen from hydrogen chloride and mixtures of the latter with chlorine and/or chloral, at a temperature of from 190° to 230° C., with a fluidized catalyst comprising copper chloride deposited on a granular support, the support comprising alumina in the crystallographic form eta, having a total volume of pores of from 0.3 to 0.5 ml/g with at least 90% of the said volume attributable to pores with a radius of less than 40 Å, and a surface area of from 250 to 400 m$^2$/g with at least 90% of the said surface area attributable to pores with a radius of less than 30 Å, these values being determined according to the B.E.T. method by absorption of nitrogen at liquid nitrogen temperature.

The catalyst used in the preparation of chlorobenzene according to the present invention, differs from those of the prior art mainly on account of the crystallographic form and the morphological characteristics of the alumina support.

Such properties of the support, together with the use of the catalyst in fluidized bed form, permit the process of the invention to be carried out with complete conversion of the halogenating agent and in the absence, or substantial absence, of phenomena of total oxidation of benzene.

The eta alumina support is preferably in the form of granules with a size of from 20 to 100 microns and has generally a bulk density of 1.10–1.15 g/cm$^3$.

Eta alumina, which may for example be obtained by heating bayerite in air, crystallizes in the cubic (spinel) system.

Preferably, the eta alumina support should be free from, or substantially free from silica and iron (silica content less than 0.01% and iron content less than 0.02% by weight) and its sodium content should be less than 0.3% by weight.

The pore volume and the surface area of the alumina support are critical, as also is the pore distribution, as these values should be within the ranges indicated above.

The best results are obtained when the alumina has a total pore volume of 0.4 ml/g, at least 90% of said volume being attributable to pores with a radius of less than 30 Å, and a surface area of about 350 m$^2$/g, at least 90% of said area being attributable to pores with a radius of less than 20 Å, these determinations being carried out according to the B.E.T. method by absorption of nitrogen at liquid nitrogen temperature ($-195°$ C.).

Preferably, the catalyst contains from 2 to 8 wt.% of copper chloride (calculated as metal), best results being obtained with a copper content of the order of 4–5 wt.%.

In fact, no appreciable advantages are obtained with a copper content of more than 8% by weight; on the other hand, copper contents of less than 2% by weight require longer residence times under the oxychlorination conditions.

The catalyst used in the process of the present invention may be prepared according to conventional methods by bringing the granular support into contact with an aqueous and/or alcoholic (for example methanolic) solution of cupric chloride.

To this end, anhydrous or hydrated cupric chloride may be used, and in each case it is preferable to use a salt of the greatest possible purity.

Thus, for example, it is convenient to use a salt having a content of cations other than copper (for example iron) of less than 2% by weight and a content of anions other than chlorine (for example nitrates) of less than 0.5% by weight.

The said cupric chloride may be dissolved in the solvent up to a concentration of about 15% by weight. The impregnation of the support may be carried out at a temperature of from ambient value (20°–25°C.) up to around 70° C., and the impregnated support may then be dried at a temperature not exceeding 200° C.

According to another embodiment, impregnation of the support and drying are carried out simultaneously by spraying the cupric chloride solution on a fluidized bed of particles of the support, operating at a temperature of the order of 130° C.

The catalyst thus obtained has the desired characteristics relating to the non-volatility of the copper salt and attrition loss of the catalyst, under the temperature conditions in which the chlorobenzene is prepared.

Therefore, it is not necessary to add to the catalyst an alkali metal chloride, normally used in the prior art in order to reduce the volatility of the cupric chloride.

According to the present invention chlorobenzene is prepared by feeding a gaseous flow containing benzene, oxygen and a halogenating agent chosen from hydrogen chloride or a mixture of this with chlorine and/or chloral to the fluidized catalyst.

In the case of chlorine being used as the halogenating agent there is obviously a chlorination of the benzene with evolution of hydrogen chloride and an oxychlorination of the benzene by the said hydrogen chloride and the oxygen fed in. The chlorination mechanism of the benzene when chloral is present in the gaseous flow is not clear. It has been experimentally ascertained that said chloral is completely converted under the reaction conditions with formation of chlorobenzene.

It is moveover convenient to use air as the source of the oxygen and to feed in from 0.1 to 0.5 atoms of chlorine, contained in the halogenating agent, for every mole of benzene.

The reason for operating with the halogenating agent in default with regard to benzene, is found in the need to limit the formation of chlorobenzenes with a degree of chlorination higher than monochlorobenzene.

Conveniently from 0.4 to 0.6 moles of oxygen are fed in for each atom of chlorine contained in the halogenating agent. The best results are obtained with a ratio of the number of moles of benzene to be chlorinated to the number of moles of oxygen to the number of chlorine atoms equal to 3:0.5:1. The benzene oxychlorination reaction is carried out at a temperature of from 190° to 230° C. and preferably of from 200° to 220° C. The reaction is generally carried out at a pressure of from 1 to 3 atm. Moreover, the residence time of the gaseous flow, measured under the temperature and pressure conditions of oxychlorination and with the reactor devoid of catalyst, is generally from 25 to 45 seconds.

By operating under the conditions described above practically complete conversion of the halogenating agent is obtained. In fact, the halogenating agent is present only in traces in the gases issuing from the oxychlorination reactor. Moreover, those secondary reactions which give rise to the conversion of benzene or its chlorinated derivatives into by-products are completely or substantially completely avoided. In particular, the total oxidation reactions which bring about the formation of carbon dioxide and water are avoided.

EXAMPLE 1

Eta alumina in granules of from 20 to 100 microns, having a bulk density of 1.13 g/cm$^3$, is used for the preparation of the catalyst.

The alumina has a total pore volume equal to 0.4 ml/g, 25% of this volume being attributable to pores with a radius of less than 12 Å and 95% of said volume being attributable to pores with a radius of less than 30 Å, as results from B.E.T. determinations.

Moreover, the alumina has a surface area of 362 m$^2$/g, 25% of this area being attributable to pores with a radius of less than 11 Å and 90% of said area being attributable to pores with a radius of less than 21 Å.

89.5 parts by weight of the said alumina, dried at 105° C., are placed in a tubular reactor, fitted with a porous plate at the bottom, and with a heating jacket.

A flow or air is injected at the base of the reactor in such a way as to ensure fluidization with a linear velocity of the gas of 4–8 cm/sec under the operating conditions, and heat is supplied so as to bring the temperature of the fluidized bed to 130° C.

Moreover, 10.6 parts by weight of cupric chloride dihydrate are dissolved in water until a solution containing 15% by weight of the salt is formed, and the solution thus obtained is sprayed onto the fluid bed, the feed rate of the solution being regulated so as not to change the temperature of the bed to values below 120° C.

Throughout the whole operation of spraying the cupric chloride solution special care is taken to keep the temperature in the fluidized bed uniform and to avoid the formation of lumps.

Finally, the catalyst is cooled and discharged.

EXAMPLE 2

Abous 2,800 grams of the catalyst prepared as described in Example 1 are placed within a tubular reactor having an internal diameter of 40 mm. At the bottom of the reactor is fed in a gaseous flow consisting of hydrogen chloride, benzene and air in which the molar ratios of hydrogen chloride:benzene:oxygen are of 0.66:2:0.33.

The supply is regulated in such a way as to ensure a linear velocity of the gas equal to 10 cm/sec, said velocity being calculated on the empty tube, at the temperature and pressure indicated below.

Moreover, the reaction is carried out with a fluidized catalyst, at a temperature of 200° C., at a pressure of 1 atm and with a residence time of 26 seconds.

By operating under these conditions practically no hydrogen chloride is found in the gases issuing at the top of the reactor and about 30% of the benzene is converted.

The chlorobenzenes produced consist of 84% in moles of monochlorobenzene and 16% in moles of dichlorobenzene. The dichlorobenzene produced consists of a mixture of para and ortho isomers in a ratio of about 2:1.

EXAMPLE 3

The test of Example 2 is repeated, using a molar ratio of hydrogen chloride:benzene:oxygen equal to 0.88:2:0.44.

In these conditions about 38% of the benzene is converted and practically no hydrogen chloride is found in the gases leaving the reactor. The chlorobenzenes produced consist of 70% in moles of monochlorobenzene and 24% in moles of dichlorobenzene.

EXAMPLE 4

The test of Example 2 is repeated, using a molar ratio of hydrogen chloride:benzene:oxygen equal to 0.94:2:0.47.

Moreover, the reaction temperature is 220° C. and the residence time 36 seconds.

Under these conditions the benzene conversion is about 40% and the other results are similar to those of Example 3.

EXAMPLE 5

The test of Example 2 is repeated, using a molar ratio of hydrogen chloride:benzene:oxygen equal to 0.56:2:0.28.

Moreover, the reaction temperature is 190° and the residence time 27 seconds.

Under these conditions about 26% of the benzene is converted and hydrogen chloride is present only as traces in the gases discharged from the reactor.

The chlorobenzenes produced consist of 84% in moles of monochlorobenzene and 16% in moles of dichlorobenzene.

EXAMPLE 6

This test is carried out as in Example 2, using a gaseous flow consisting of benzene, air and a chlorinating mixture consisting of hydrogen chloride, chlorine and chloral in a molar ratio of 45:45:10.

Moreover, there is maintained in the gaseous flow a ratio between the number of chlorine atoms (in the chlorination mixture), the moles of benzene and the moles of oxygen equal to 0.88:2:0.44.

The reaction is also carried out at 200° C., with a gas velocity equal to 10 cm/sec. and with a residence time of 20 seconds. Under these conditions about 38% of the benzene is converted and the chlorinating agents are practically absent from the reaction gases.

The chlorobenzenes produced consist of 75% in moles of monochlorobenzene and 25% in moles of dichlorobenzene.

In all the experimental Examples described only traces of the total oxidation products of benzene are found in the reaction gases.

What we claim is:

1. A method for the production of chlorobenzene, which comprises contacting a gaseous flow comprising benzene, oxygen and a halogenating agent selected from the group consisting of hydrogen chloride and mixtures of the latter with chlorine and/or chloral, at a temperature of from 190° to 230° C., with a fluidized catalyst comprising copper chloride deposited on a granular support, the support consisting essentially of alumina in the crystallographic form eta, having a total volume of pores of from 0.3 to 0.5 ml/g with at least 90% of the said volume attributable to pores with a radius of less than 40 Å, and a surface area of from 250 to 400 m$^2$/g with at least 90% of the said surface area attributable to pores with a radius of less than 30 Å, these values being determined according to the B.E.T. method by absorption of nitrogen at liquid nitrogen temperature.

2. The method of claim 1, in which said gaseous flow contains from 0.1 to 0.5 chlorine atoms, contained in the halogenating agent, for each mole of benzene and from 0.4 to 0.6 moles of oxygen for each of said chlorine atoms.

3. The method of claim 1, wherein said gaseous flow is contacted with said catalyst at a pressure of from 1 to 3 Atmospheres.

4. The method of claim 1, wherein said gaseous flow is contacted with said catalyst at a temperature of from 200° to 220° C.

5. The method of claim 1, wherein the residence time of the gaseous flow under the reaction conditions is from 25 to 45 seconds.

6. The method of claim 1, wherein said eta alumina has a total volume of pores of 0.4 ml/g with at least 90% of said volume attributable to pores with a radius of less than 30 Å, and a surface area of about 350 m$^2$/g with at least 90% of said area attributable to pores with a radius of less than 20 Å.

7. The method of claim 1, wherein said alumina is in the form of granules of from 20 to 100 microns in size.

8. The method of claim 1, wherein said catalyst contains from 2 to 8% by weight of copper calculated as metal.

* * * * *